United States Patent
Kim et al.

(10) Patent No.: US 10,952,613 B2
(45) Date of Patent: Mar. 23, 2021

(54) STROKE DIAGNOSIS AND PROGNOSIS PREDICTION METHOD AND SYSTEM

(71) Applicants: JLK INSPECTION, Cheongju-si (KR); DONGGUK UNIVERSITY INDUSTRY-ACADEMIC COOPERATION FOUNDATION, Seoul (KR)

(72) Inventors: Dong Eog Kim, Seoul (KR); Won Tae Kim, Suwon-si (KR); Shin Uk Kang, Seoul (KR); Myung Jae Lee, Seoul (KR); Dong-min Kim, Seoul (KR)

(73) Assignees: JLK INSPECTION, Cheongju-si (KR); DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 16/343,776

(22) PCT Filed: Sep. 14, 2017

(86) PCT No.: PCT/KR2017/010091
§ 371 (c)(1),
(2) Date: Apr. 22, 2019

(87) PCT Pub. No.: WO2018/074739
PCT Pub. Date: Apr. 26, 2018

(65) Prior Publication Data
US 2019/0246904 A1 Aug. 15, 2019

(30) Foreign Application Priority Data
Oct. 20, 2016 (KR) .................... 10-2016-0136308

(51) Int. Cl.
*A61B 5/00* (2006.01)
*G06T 7/00* (2017.01)
(Continued)

(52) U.S. Cl.
CPC ............ *A61B 5/0042* (2013.01); *A61B 5/055* (2013.01); *A61B 5/7246* (2013.01);
(Continued)

(58) Field of Classification Search
CPC ... A61B 5/0042; A61B 5/7267; A61B 5/7275; A61B 5/055; A61B 5/7246;
(Continued)

(56) References Cited

U.S. PATENT DOCUMENTS

| 2009/0034812 A1* | 2/2009 | Nowinski | A61B 5/7425 382/131 |
| 2009/0129649 A1 | 5/2009 | Djeridane | |

(Continued)

FOREIGN PATENT DOCUMENTS

| KR | 10-2013-0021450 A | 3/2013 |
| KR | 10-2014-0028534 A | 3/2014 |

(Continued)

OTHER PUBLICATIONS

Stier, Noah, et al. "Deep learning of tissue fate features in acute ischemic stroke." 2015 IEEE international conference on bioinformatics and biomedicine (BIBM). IEEE, 2015. (Year: 2015).*

(Continued)

*Primary Examiner* — Amandeep Saini
(74) *Attorney, Agent, or Firm* — Revolution IP, PLLC

(57) ABSTRACT

A stroke diagnosis and prognosis prediction system includes: an image acquisition unit configured so as to receive a plurality of images including at least a part of a human brain; an image alignment unit for aligning the plurality of images on the basis of a standard brain image;
(Continued)

a lesion area detection and mapping unit for respectively detecting lesion areas from the plurality of images, and mapping the detected lesion areas so as to generate one mapping image; a matching and correction unit, which scales a mapping image so as to match the same to the standard brain image and performs image correction on the mapping image; a three-dimensional image generation unit storing the mapping image in a three-dimensional data space, thereby generating a three-dimensional lesion image; and a stroke diagnosis unit for diagnosing a stroke on the basis of the three-dimensional lesion image.

8 Claims, 5 Drawing Sheets

(51) Int. Cl.
*A61B 5/055* (2006.01)
*G06N 3/02* (2006.01)
*G16H 50/20* (2018.01)

(52) U.S. Cl.
CPC .......... *A61B 5/7267* (2013.01); *A61B 5/7275* (2013.01); *A61B 5/7425* (2013.01); *G06N 3/02* (2013.01); *G06T 7/0014* (2013.01); *G16H 50/20* (2018.01); *G06T 2200/04* (2013.01); *G06T 2207/10088* (2013.01); *G06T 2207/20084* (2013.01); *G06T 2207/30016* (2013.01)

(58) Field of Classification Search
CPC . A61B 5/7425; A61B 5/02014; A61B 5/4076; A61B 2576/026; A61B 5/4064; G06N 3/02; G06N 3/0454; G16H 50/20; G16H 50/30; G16H 30/40; G06T 7/0014; G06T 2200/04; G06T 2207/30016; G06T 2207/20084; G06T 2207/10088
USPC .......................................................... 382/128
See application file for complete search history.

(56) References Cited

U.S. PATENT DOCUMENTS

2015/0313566 A1* 11/2015 Diers .................. A61B 6/5217
378/63
2016/0302689 A1 10/2016 Kang et al.

FOREIGN PATENT DOCUMENTS

| KR | 10-2015-0057045 A | 5/2015 |
| KR | 10-2015-0094877 A | 8/2015 |
| KR | 10-2015-0098119 A | 8/2015 |
| KR | 10-2015-0108701 A | 9/2015 |
| KR | 10-2016-0058812 A | 5/2016 |

OTHER PUBLICATIONS

International Search Report for PCT/KR2017/010091 dated Jan. 22, 2018 from Korean Intellectual Property Office.

* cited by examiner

STROKE DIAGNOSIS AND PROGNOSIS PREDICTION METHOD AND SYSTEM

TECHNICAL FIELD

The present invention relates to a stroke diagnosis and prognosis prediction method and, more particularly, to a stroke diagnosis and prognosis prediction method and system capable of precisely diagnosing a stroke and reliably predicting the state of a stroke patient.

BACKGROUND ART

A stroke (or apoplexy) generally refers to a local neurologic loss symptom suddenly occurring due to the abnormality of a cerebral blood flow. The stroke is the term of a symptom and is called a cerebrovascular disease when it is called as a medical disease. The stroke is basically divided into cerebral infarction and brain hemorrhage.

In conventional stroke diagnosis, an expert medical specialist determines the cause of a stroke and evaluates the severity of the stroke. A method of classifying a stroke cause, used as an international criterion, is a Trial of Org 10172 in Acute Stroke Treatment (TOAST) criterion. The TOAST classification method is a classification method that is most commonly used so far. The causes of a stroke are classified into large artery atherosclerosis, cardioembolism, small artery occlusion, other causes, and an undetermined cause depending on a pathogenesis occurred.

Furthermore, a degree (severity) of an initial neurologic loss has been known to be very important as a factor to determine stroke prognosis. Several criteria are used to measure the initial neurologic loss degree, but are insufficient to satisfy all validity, reliability and measurement easiness. The evaluation of the severity is performed by NIHSS.

The National Institute of Health Stroke Scale (NIHSS) is most used in Korea because it has been known to have high validity and reliability. In clinic research, it is necessary to quantitatively measure the severity of a neurologic loss. In actual clinic, however, the severity of a neurologic loss is not quantitatively measured and analyzed, but is descriptively measured and recorded. Furthermore, there is a method of evaluating the state after stroke treatment using a mRS criterion after three months.

Meanwhile, to evaluate the nature of a tissue disease and diagnose the nature of a pathological disease or a scheme therefor has been proposed as a conventional technology. For example, conventional technologies include Korean Patent Application Publication No. 10-2016-0058812 (Feb. 25, 2016) entitled "Image analysis techniques for diagnosing diseases", Korean Patent Application Publication No. 10-2015-0098119 (Aug. 27, 2015) entitled "System and method for removing false positive lesion candidate in medical image", Korean Patent Application Publication No. 10-2015-0108701 (Sep. 30, 2015) entitled "Apparatus and method for visualizing anatomic elements in a medical image."

Korean Patent Application Publication No. 10-2016-0058812 discloses a scheme for evaluating the nature of a tissue disease, diagnosing the nature of a pathological disease or evaluating prognosis thereof or a danger thereof. The scheme includes an image acquiring module configured to receive an image including at least some of an animal or human tissue, a delineation module configured to display an analysis area in the obtained image, a feature extraction module configured to extract quantitative information from the analysis area, and a machine learning module configured to receive the extracted information in order to evaluate the nature of a tissue disease and to apply at least one detection algorithm.

The above-described conventional documents disclose a technology for performing diagnosis according to a common disease or lesion rather than for the diagnosis of a stroke and the prediction of prognosis.

Meanwhile, for the diagnosis of a stroke and the prediction of prognosis, all of massive MRI image data and patient clinic information must be considered. Accordingly, a lot of time for diagnosis is consumed, and a deviation in the diagnosis results may be great depending on a skill level of a medical team.

Accordingly, there is a need for a method capable of providing results having a minimized deviation in the diagnosis results while rapidly diagnosing a stroke, improving the accuracy of the final diagnosis and prognosis prediction of a medical team, and thus performing optimal medical measures.

DISCLOSURE

Technical Problem

The present invention has been made to solve the above problems occurring in the prior art and an object of the present invention is to provide a stroke diagnosis and prognosis prediction method capable of accurately diagnosing a stroke and reliably predicting the state of a stroke patient.

Another object of the present invention is to provide a stroke diagnosis and prognosis prediction system using the above-described stroke diagnosis and prognosis prediction method.

Technical Solution

A stroke diagnosis and prognosis prediction system according to an aspect of the present invention for achieving the object includes an image acquisition unit configured to receive a plurality of images including at least some of a human brain; an image array unit arranging the plurality of images based on a standard brain image; a lesion area detection and mapping unit detecting lesion areas in the plurality of images, respectively, and generating a single mapping image by mapping the plurality of images to the detected lesion areas; a matching and correction unit matching the mapping image with the standard brain image by scaling the mapping image and performing image correction on the mapping image; a three-dimensional image generation unit generating a three-dimensional lesion image by storing the mapping image in a three-dimensional data space; and a stroke diagnosis unit diagnosing a stroke based on the three-dimensional lesion image.

The lesion area detection and mapping unit may match the mapped location of a lesion with the standard brain image based on matching location information of the plurality of images.

The 3-D image generation unit may binarize pixel information of the three-dimensional lesion image depending on whether a lesion is present with respect to the lesion image before the lesion image is generated, and may adjust the size of the lesion image.

The stroke diagnosis unit may extract the features of the stored 3-D lesion image using a deep neural network, and may diagnose the stroke by classifying a cause of the stroke based on the extracted features of the 3-D lesion image.

The deep neural network may include a three-dimensional convolutional neural network (CNN).

The stroke diagnosis unit may classify a severity of the diagnosed stoke.

The stroke diagnosis unit may predict a critical risk within three weeks from the lesion image and predict a patient state after a given time.

The plurality of images may be MRI images. The MRI images may include diffusion weighted imaging (DWI), a fluidattenuated inversion recovery (FLAIR) image, a gradient echo (GE) image, and a T2 weighted image (T2).

A method according to an aspect of the present invention for achieving the object includes the steps of obtaining a plurality of images including at least some of a human brain; arranging the plurality of images based on a standard brain; detecting lesion areas in the plurality of images, respectively, and generating a single mapping image by mapping the plurality of images to the detected lesion areas; matching the mapping image with a standard brain image by scaling the mapping image and performing image correction on the mapping image; generating a three-dimensional lesion image by storing the mapping image in a three-dimensional data space; and diagnosing a stroke based on the three-dimensional lesion image.

In one embodiment, in the step of generating the single mapping image, the mapped location of the lesion may be matched with the standard brain image based on location information of the matching.

In one embodiment, the stroke diagnosis and prognosis prediction method may further include the steps of binarizing pixel information of the three-dimensional lesion image depending on whether a lesion is present with respect to the lesion image before the lesion image is generated, and adjusting the size of the lesion image.

In one embodiment, in the step of diagnosing the stroke, the features of information of the stored three-dimensional lesion image may be extracted using a three-dimensional convolutional neural network (CNN).

In one embodiment, in the step of diagnosing the stroke, a severity of the diagnosed stoke may be classified.

In one embodiment, in the step of diagnosing the stroke, a critical risk within three weeks from the lesion image may be predicted, and a patient state after a given time may be predicted.

Advantageous Effects

According to the embodiments of the present invention, quantitative and statistical results can be provided by visualizing the cause and severity of a stroke along with accuracy for each class, and they become a reference to a doctor's final diagnosis and enable demonstrative description for a patient.

MODE FOR INVENTION

Figure 1:
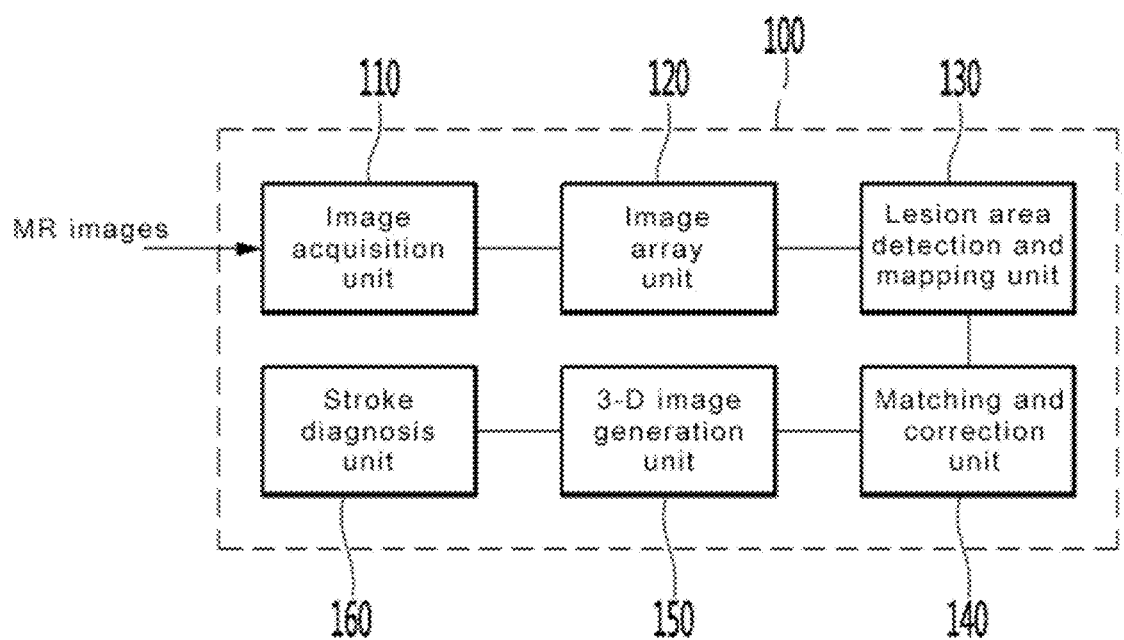
FIG. 1 is a block diagram of a stroke diagnosis and prognosis prediction system according to an embodiment of the present invention.

The present invention may be modified in various ways and may have various embodiments. Specific embodiments are to be illustrated in the drawings and are to be described the detailed description. The effects and characteristics of the present invention and a method for achieving them will become evident with reference to the embodiments described in detail along with the drawings. However, the present invention is not limited to the following embodiments, but may be implemented in various forms.

Hereinafter, the embodiments of the present invention are described in detail with reference to the accompanying drawings. In the drawings, the same or corresponding elements are assigned the same reference numerals, and a redundant description thereof is omitted.

FIG. 1 is a block diagram of a stroke diagnosis and prognosis prediction system according to an embodiment of the present invention.

Referring to FIG. 1, the stroke diagnosis and prognosis prediction system 100 according to an embodiment of the present invention includes an image acquisition unit 110, an image array unit 120, a lesion area detection and mapping unit 130, a matching and correction unit 140, a three-dimensional (3-D) image generation unit 150, and a stroke diagnosis unit 160.

The image acquisition unit 110 obtains medical images used to diagnose a stroke. Specifically, the image acquisition unit 110 obtains magnetic resonance imaging (MRI) from a medical imaging device. In one embodiment, the MR images include diffusion weighted imaging (DWI), a fluidattenuated inversion recovery (FLAIR) image, a gradient echo (GE) image, and a T2 weighted image (T2). In other words, the image acquisition unit 110 uses MR images, obtained using four different sequences of a diffusion weighted image (DWI), a T2 weighted image, a FLAIR image, and a T1 weighted image, as MR images used for diagnosis. The image acquisition unit 110 transmits the obtained medical images to the image array unit 120.

The image array unit 120 standardizes a plurality of images based on the coordinates of a Montreal neurological institute (MNI) standard brain image, and corrects the location and direction of a brain into a linear movement and rotation based on a standard brain image that may be represented as coordinates. That is, the image array unit 120 performs standardization on input MR images based on an MNI template. In this case, the standard brain image is a comparison image used for the diagnosis of a stroke, and is used to determine whether a lesion is present and the severity of a lesion when a patient brain image is analyzed. The standard brain image may be different by race, sex or age. For example, the standard brain image may be a Korean's standard brain image.

The lesion area detection and mapping unit 130 detects a lesion area in a plurality of images, and performs mapping. Specifically, the lesion area detection and mapping unit 130 detects a lesion area in each of the plurality of images and generates a single mapping image by mapping the images to the detected lesion areas. Furthermore, the lesion area detection and mapping unit 130 matches the mapped location of the lesion with the standard brain image based on matching location information of the plurality of images. For example, the lesion area detection and mapping unit 130 detects a lesion area so that information of the lesion area is output to an MNI space in a binary format.

The matching and correction unit 140 matches the mapping image with the standard brain image by scaling the mapping image, and performs image correction on the mapping image. Specifically, the matching and correction unit 140 modifies the size of a patient's brain linearly or non-linearly and matches it with the standard brain image. In this case, the matching and correction unit 140 matches the location of a lesion, mapped based on the location information of matching, with the coordinates of the standard brain image, and then performs image correction. The image correction includes an operation of removing noise included in an image or adjusting brightness.

The 3-D lesion image generation unit 150 generates a 3-D lesion image by storing the mapping image in a 3-D data space. Furthermore, the 3-D lesion image generation unit 150 may perform pre-processing on the mapping image of the lesion matched with the standard brain coordinates. Specifically, the 3-D lesion image generation unit 150 binarizes pixel information into {1, 0} depending on whether a lesion is present when the mapping image is pre-processed, and may adjust the size of a lesion image, if necessary. For example, the size of the lesion image may be reduced to ½ or ¼ of the original size. For example, the 3-D lesion image generation unit 150 rearranges all images based on an average image, standardizes a patient's brain based on the coordinates of the Montreal Neurological Institute (MNI) standard brain image, and performs pre-processing on image data through a series of processes of smoothing data values using a normal distribution kernel of 8 mm in each of the length, breadth, and height.

MR images obtained from respective sequences are reconfigured into a 3-D data space, and the area of each lesion can be displayed as a 3-D coordinate space. Furthermore, weight is assigned to the MR image obtained from each sequence depending on a degree of importance in the pre-processing step, and the MR images are integrated into a single lesion map in the 3-D space.

Figure 2:
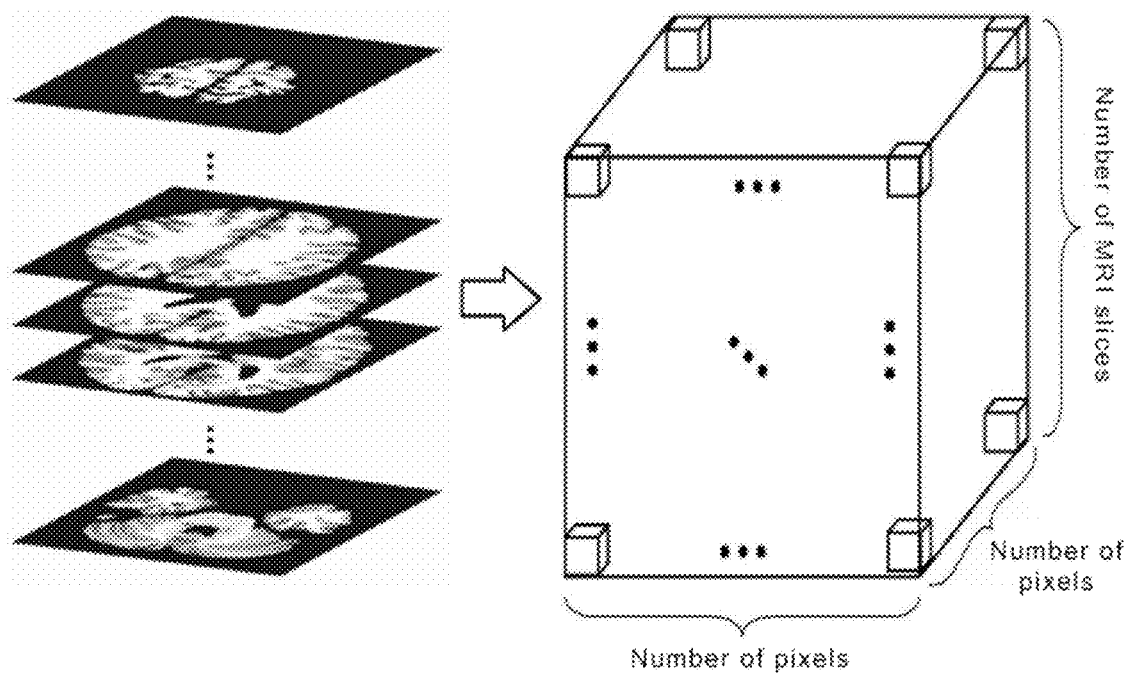
FIG. 2 is a view showing a three-dimensional (3-D) data space in a diagram form according to the present invention.

The 3-D lesion image generation unit 150 generates a 3-D lesion image by writing a 3-D data space for each sequence for obtaining an image using mapping images on which required pre-processing has been performed and storing the images in the 3-D data space. FIG. 2 is a view showing a 3-D data space in a diagram form according to the present invention. As shown in FIG. 2, the number of horizontal pixels×the number of vertical pixels×the number of included slices of a brain of each image after matching with a standard brain have been allocate to the 3-D data storage space. A value stored in a pooling layer is an average value in the case of an image having only lesion information, and is a maximum value in the case of the original MR data.

The stroke diagnosis unit 160 diagnoses a stroke by analyzing a stroke cause based on the 3-D lesion image.

Figure 3:
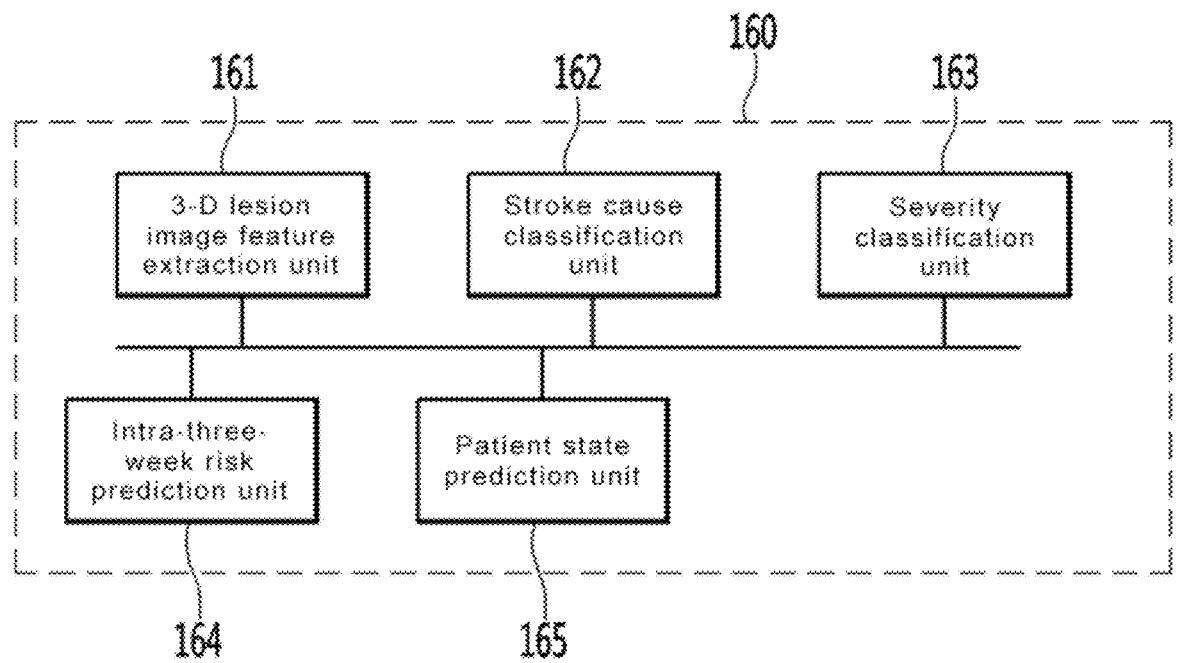
FIG. 3 shows a block diagram of a stroke diagnosis unit according to an embodiment of the present invention.

FIG. 3 shows a block diagram of the stroke diagnosis unit according to an embodiment of the present invention.

Referring to FIG. 3, the stroke diagnosis unit 160 includes a 3-D lesion image feature extraction unit 161, a stroke cause classification unit 162, a severity classification unit 163, an intra-three-week risk prediction unit 164 and a patient state prediction unit 165.

Figure 4:
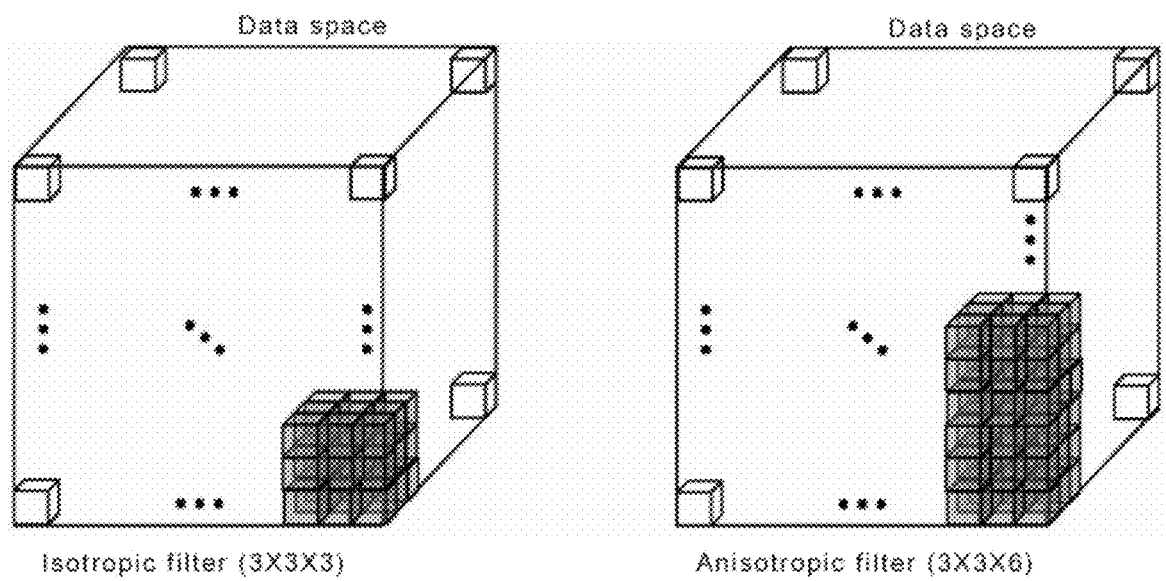
FIG. 4 is a diagram showing an example of a deep neural network.

The 3-D lesion image feature extraction unit 161 may extract the features of a 3-D lesion image stored in a 3-D data storage space using a deep neural network. FIG. 4 is a diagram showing an example of a deep neural network. As shown in FIG. 4, in a process of designing the deep neural network, the size of a data filter is set isotropically or anisotropically depending on classification and analysis contents. In other words, a filter configuration may be designed isotropically and anisotropically for each sequence, if necessary, in an image and thickness direction. The deep neural network may be a 3-D convolutional neural network (CNN).

The stroke cause classification unit 162 may diagnose a stroke by classifying a stroke cause based on the extracted features of the 3-D lesion image. A TOAST classification criterion, that is, an international criterion, is used for the classification of the cause of a stroke. Specifically, the stroke cause classification unit 162 basically classifies the causes of a stroke chiefly into large artery atherosclerosis, cardioembolism, and small artery occlusion from among classifications based on the TOAST classification, that is, an international criterion. If it is difficult to determine the cause of a stroke based on any one classification criterion based on each classification result, the cause of a stroke is classified as other diseases.

The severity classification unit 163 may classify the severity of the diagnosed stoke. The classification of the severity may be performed based on NIHSS classification, that is, an international criterion. The severity classification unit 163 configures a classification criterion based on an NIHSS criterion, that is, an international criterion, in order to classify the severity of a stroke, and classifies the severity as the following four steps for the simplicity of a determination. The severity classification unit 163 classifies a criterion, corresponding to 0 of NIHSS, as "no symptom", classifies the range of scores 1~4 of NIHSS as "severity low", classifies the range of scores 5~15 of NIHSS as "severity normal", classifies the range of scores 16~20 of NIHSS as "severity danger", and classifies the range of scores 21~42 of NIHSS as "severity severe."

The intra-three-week risk prediction unit 164 predicts a critical risk within three weeks from the lesion image. The intra-three-week risk prediction unit 164 predicts a risk of the worsening possibility of a patient state within three weeks after the hospital stay of the patient as a percentage, and it classifies 90% or more of the rate of a risk as "risk very high", classifies 70%~90% of the rate of a risk as "risk high", classifies 30%~70% of the rate of a risk as "risk normal", and classifies less than 30% of the rate of a risk as "risk low."

Furthermore, the patient state prediction unit 165 predicts a patient state after a given time. Specifically, the patient state prediction unit 165 performs patient state classification after three months based on mRS classification regulations, that is, an international criterion. The stroke cause classification unit 162, the severity classification unit 163, and the patient state prediction unit 165 may determine the scoring range of each classification criterion based on an algorithm configuration and use the determined scoring range.

As described above, stroke classification and analyzed contents according to the stroke diagnosis and prognosis prediction system of the present invention are visualized along with accuracy for each class of classification when a medical certificate and prognosis prediction report are written, and provide quantitative and statistical results. They become a doctor's final diagnosis and enable demonstrative description for a patient.

As described above, the present invention provides a platform capable of classifying the cause and severity of each stroke using artificial intelligence diagnosis and prediction software trained using a deep learning algorithm and predicting a worsening risk within three weeks after a hospital stay and a patient state after three months.

Figure 5:
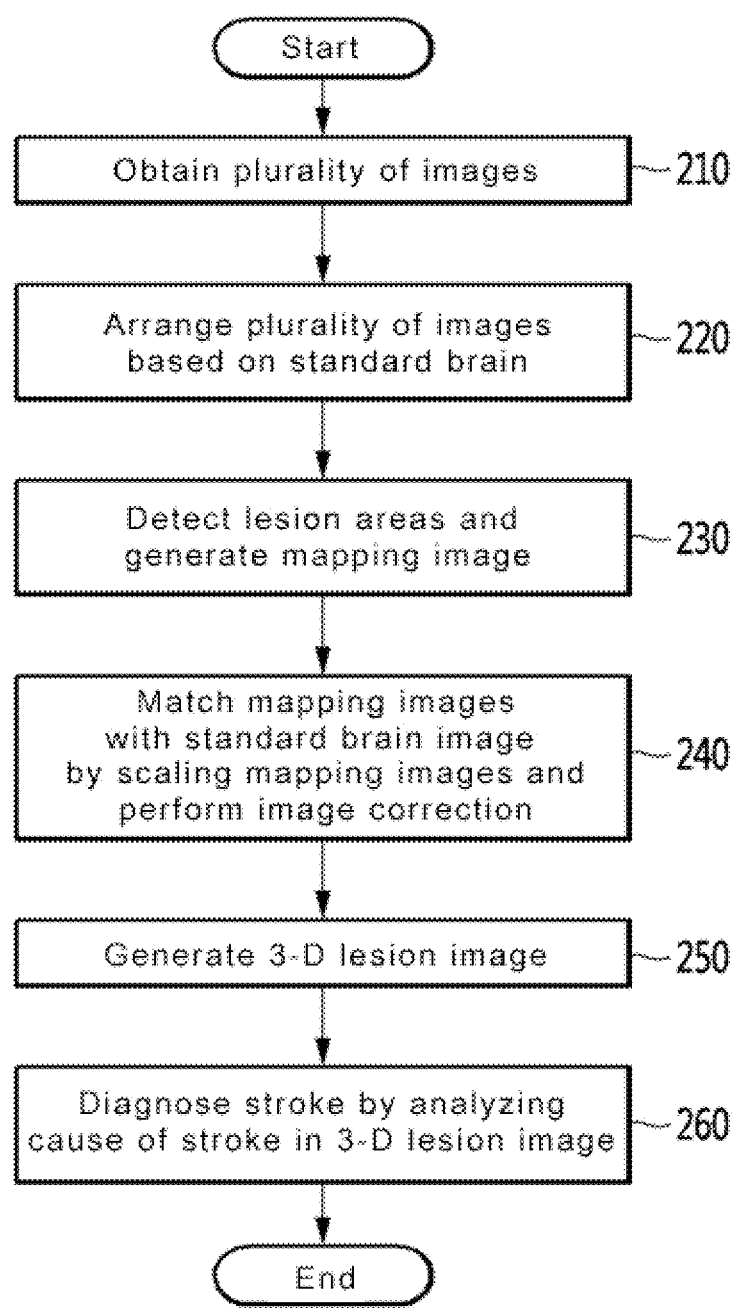
FIG. 5 is a flowchart of a stroke diagnosis and prognosis prediction method according to an embodiment of the present invention.

FIG. 5 is a flowchart of a stroke diagnosis and prognosis prediction method according to an embodiment of the present invention. First, the stroke diagnosis and prognosis prediction system obtains a plurality of images from at least some of a human brain at step 210. The plurality of images may be MR images. The MR images include diffusion weighted imaging, a fluidattenuated inversion recovery (FLAIR) image, a gradient echo image, and a T2 weighted image.

Next, the stroke diagnosis and prognosis prediction system arranges the plurality of images based on a standard brain at step 220. Specifically, the stroke diagnosis and prognosis prediction system standardizes the plurality of images based on the coordinates of a Montreal neurological institute (MNI) standard brain image, and corrects the location and direction of a brain into a linear movement and rotation based on the standard brain image that may be represented as coordinates.

At step 230, the stroke diagnosis and prognosis prediction system detects lesion areas in the plurality of images, respectively, and generates a single mapping image by mapping the images to the detected lesion areas.

Thereafter, at step 240, the stroke diagnosis and prognosis prediction system matches the mapping images with the standard brain image by scaling the mapping images, and performs image correction on the mapping image. Specifically, the stroke diagnosis and prognosis prediction system matches the size of a patient's brain with the standard brain image by modifying the size linearly or non-linearly. In this case, the location of a lesion mapped based on location information of matching is matched with the coordinates of the standard brain image, and image correction is then performed on the mapping image.

Thereafter, at step 250, the stroke diagnosis and prognosis prediction system generates a 3-D lesion image by storing the mapping image in a 3-D data space. Furthermore, although not shown, the stroke diagnosis and prognosis prediction system may perform pre-processing on the mapping image of the lesion matched with the standard brain coordinates. When the mapping image is pre-processed, the stroke diagnosis and prognosis prediction system may binarize pixel information into {1, 0} depending on whether a lesion is present, and may adjust the size of a lesion image, if necessary. In this case, the stroke diagnosis and prognosis prediction system generates the 3-D lesion image by writing a 3-D data space for each sequence for obtaining an image using the mapping images on which required pre-processing has been performed and storing the images in the 3-D data space.

Next, at step 260, the stroke diagnosis and prognosis prediction system diagnoses a stroke based on a deep neural network from the 3-D lesion image.

Figure 6:
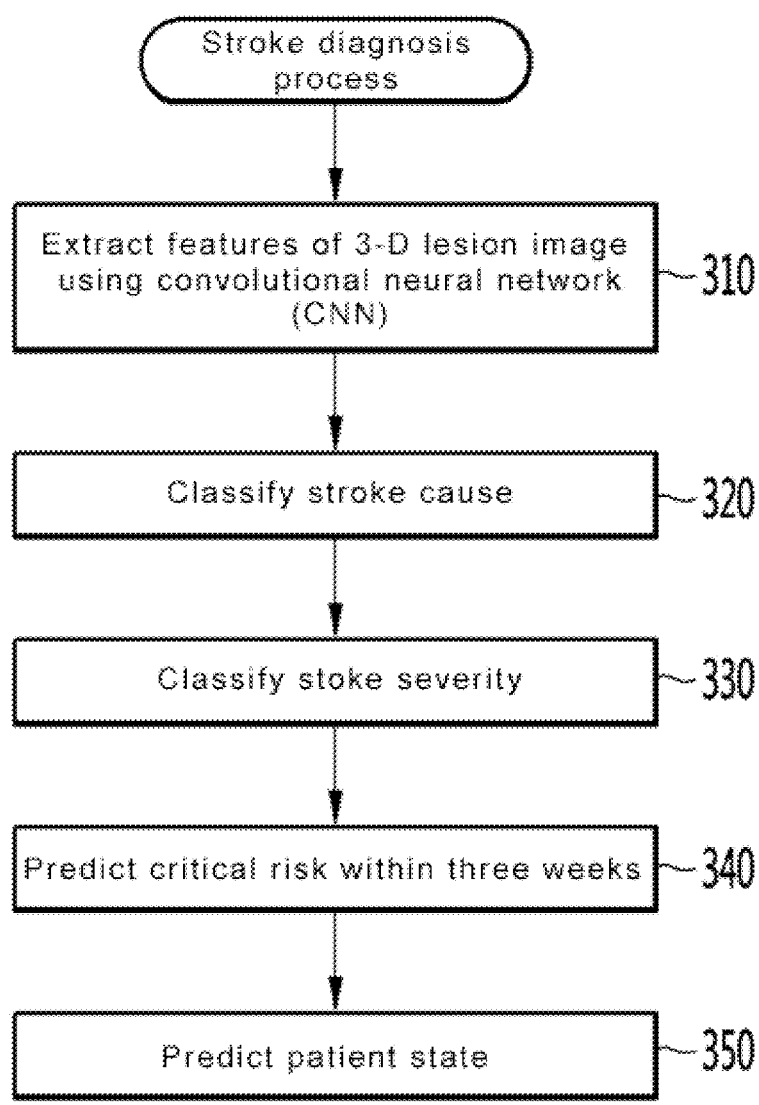
FIG. 6 shows a flowchart of a stroke diagnosis method according to an embodiment of the present invention.

FIG. 6 shows a flowchart of a stroke diagnosis method according to an embodiment of the present invention.

Referring to FIG. 6, the stroke diagnosis and prognosis prediction system may extract the features of a 3-D lesion image, stored in a 3-D data storage space, using a deep neural network at step 310. The deep neural network may be a 3-D convolutional neural network (CNN).

The stroke diagnosis and prognosis prediction system classifies a stroke cause based on the extracted features of the 3-D lesion image at step 320. A TOAST classification criterion, that is, an international criterion is used for the classification of the stroke cause. Furthermore, the stroke diagnosis and prognosis prediction system classifies the severity of the diagnosed stoke at step 330. The classification of the severity may be performed based on NIHSS classification, that is, an international criterion.

The stroke diagnosis and prognosis prediction system predicts a critical risk within three weeks from the lesion image at step 340. Specifically, at step 340, the stroke diagnosis and prognosis prediction system predicts a risk of the worsening possibility of a patient state within three weeks after the hospital stay of the patient as a percentage, and it classifies 90% or more of the rate of a risk as "risk very high", classifies 70%~90% of the rate of a risk as "risk high", classifies 30%~70% of the rate of a risk as "risk normal", and classifies less than 30% of the rate of a risk as "risk low."

Furthermore, the stroke diagnosis and prognosis prediction system predicts a patient state after a given time at step 350. Specifically, the stroke diagnosis and prognosis prediction system performs patient state classification after three months based on mRS classification regulations, that is, an international criterion.

According to the embodiment of the present invention, there is provided the platform capable of classifying the cause and severity of each stroke using artificial intelligence diagnosis and prediction software trained using a deep learning algorithm and predicting a worsening risk within three weeks after a hospital stay and a patient state after three months.

Accordingly, according to the embodiment of the present invention, a stroke can be accurately diagnosed, and the state of a stroke patient can be reliably predicted.

Meanwhile, although the detailed embodiments have been described in the detailed description of the disclosure, the disclosure may be modified in various ways without departing from the scope of the disclosure. Accordingly, the scope of the disclosure should not be limited to the above-described embodiments, but should be defined by not only the claims, but equivalents thereof.

The invention claimed is:

1. A stroke diagnosis and prognosis prediction system in a stroke diagnosis and prognosis prediction method, the system comprising:
  an image acquisition unit receiving a plurality of images comprising at least some of a human brain;
  an image array unit arranging the plurality of images based on a standard brain image;
  a lesion area detection and mapping unit detecting lesion areas in the plurality of images, respectively, and generating a single mapping image by mapping the plurality of images to the detected lesion areas;
  a matching and correction unit matching the mapping image with the standard brain image by scaling the mapping image and performing image correction on the mapping image;
  a three-dimensional image generation unit generating a three-dimensional lesion image by storing the mapping image in a three-dimensional data space; and
  a stroke diagnosis unit diagnosing a stroke based on the three-dimensional lesion image,
  wherein the stroke diagnosis unit includes:
  a 3-D lesion image feature extraction unit extracting the features of the three-dimensional lesion image stored in the three-dimensional data space using a deep neural network;
  a stroke cause classification unit diagnosing a stroke by classifying a stroke cause based on the extracted features of the three-dimensional lesion image;

a severity classification unit classifying the severity of the diagnosed stoke;

an intra-three-week risk prediction unit predicting a risk of the worsening possibility of a patient state within three weeks after the hospital stay of the patient as a percentage; and a patient state prediction unit predicting a patient state after three months based on mRS classification regulations, wherein the intra-three-week risk prediction unit classifies 90% or more of the rate of a risk as risk very high, classifies 70%~90% of the rate of a risk as risk high, classifies 30%~70% of the rate of a risk as risk normal, and classifies less than 30% of the rate of a risk as risk low.

2. The stroke diagnosis and prognosis prediction system of claim 1, wherein the lesion area detection and mapping unit matches a mapped location of a lesion with the standard brain image based on matching location information of the plurality of images.

3. The stroke diagnosis and prognosis prediction system of claim 1, wherein the three-dimensional image generation unit binarizes pixel information of the three-dimensional lesion image depending on whether a lesion is present with respect to the lesion image before the lesion image is generated, and adjusts a size of the lesion image.

4. The stroke diagnosis and prognosis prediction system of claim 1, wherein the plurality of images comprises MRI images.

5. The stroke diagnosis and prognosis prediction system of claim 4, wherein the MRI images comprise diffusion weighted imaging (DWI), a fluid attenuated inversion recovery (FLAIR) image, a gradient echo (GE) image, and a T2 weighted image (T2).

6. A stroke diagnosis and prognosis prediction method, comprising steps of:

obtaining a plurality of images comprising at least some of a human brain;

arranging the plurality of images based on a standard brain;

detecting lesion areas in the plurality of images, respectively, and generating a single mapping image by mapping the plurality of images to the detected lesion areas;

matching the mapping image with a standard brain image by scaling the mapping image and performing image correction on the mapping image;

generating a three-dimensional lesion image by storing the mapping image in a three-dimensional data space; and extracting features of the three-dimensional lesion image using a deep neural network and diagnosing a stroke based on a deep neural network trained using the extracted three-dimensional lesion image, wherein the extracting features of the three-dimensional lesion image step includes:

extracting the features of the three-dimensional lesion image stored in the three-dimensional data space using a deep neural network;

diagnosing a stroke by classifying a stroke cause based on the extracted features of the three-dimensional lesion image;

classifying the severity of the diagnosed stoke;

predicting a risk of the worsening possibility of a patient state within three weeks after the hospital stay of the patient as a percentage, wherein the percentage classifies 90% or more of the rate of a risk as risk very high, classifies 70%~90% of the rate of a risk as risk high, classifies 30%~70% of the rate of a risk as risk normal, and classifies less than 30% of the rate of a risk as risk low; and predicting a patient state after three months based on mRS classification regulations.

7. The stroke diagnosis and prognosis prediction method of claim 6, wherein the step of generating the single mapping image comprises a step of matching a mapped location of the lesion with the standard brain image based on location information of the matching.

8. The stroke diagnosis and prognosis prediction method of claim 6, further comprising steps of:

binarizing pixel information of the three-dimensional lesion image depending on whether a lesion is present with respect to the lesion image before the lesion image is generated, and adjusting a size of the lesion image.

* * * * *